United States Patent [19]

Yamaguchi

[11] Patent Number: 4,768,519

[45] Date of Patent: Sep. 6, 1988

[54] BLOOD PRESSURE MEASUREMENT APPARATUS

[75] Inventor: Keiji Yamaguchi, Shimizu, Japan

[73] Assignee: Terumo Corporation, Tokyo, Japan

[21] Appl. No.: 863,421

[22] Filed: May 15, 1986

[30] Foreign Application Priority Data

May 16, 1985 [JP] Japan .............................. 60-102575

[51] Int. Cl.$^4$ ............................................... A61B 5/02
[52] U.S. Cl. .............................. 128/680; 364/413.03
[58] Field of Search ............................... 128/680–683; 364/415, 417

[56] References Cited

U.S. PATENT DOCUMENTS

| | | |
|---|---|---|
| 3,707,959 | 1/1973 | Wilton-Davies . |
| 4,313,445 | 2/1982 | Georgi .................. 128/682 X |
| 4,475,557 | 10/1984 | Hatschek et al. ............ 128/660 X |
| 4,501,281 | 2/1985 | Furukawa . |
| 4,592,366 | 6/1986 | Sainomoto et al. ............ 128/680 |
| 4,677,983 | 7/1987 | Yamaguchi et al. ............ 128/680 |

Primary Examiner—Francis J. Jaworski
Attorney, Agent, or Firm—Staas & Halsey

[57] ABSTRACT

Disclosed is a blood pressure measurement apparatus in which a waveform discrimination method is used in the recognition of Korotkoff sounds in the measurement of blood pressure by auscultation. In processing executed by the apparatus, the minimum point or maximum point (C3) of a signal waveform indicative of the sound of vibration produced by a blood vessel is detected, and a maximum value or minimum value point (C2) is detected within a predetermined time region ($t_1$) the final instant of which is the point (C3). If a level difference between the point (C2) and the point (C3) is within a predetermined range, there is detected a minimum value or maximum value point (C1) within a predetermined time region ($t_2$) the final instant of which is (C2). If a level difference between the point (C1) and the point (C2) is within a predetermined range, there is detected a maximum value or minimum value point (C4) within a predetermined time region ($t_3$) the starting instant of which is the point (C3). It is then discriminated whether a level difference between the point (C4) and the point (C3) falls within a predetermined range. Control proceeds in successive fashion when each of these conditions is satisfied, with a Korotkoff sound being recognized in the signal waveform when all of these conditions are satisfied.

4 Claims, 8 Drawing Sheets

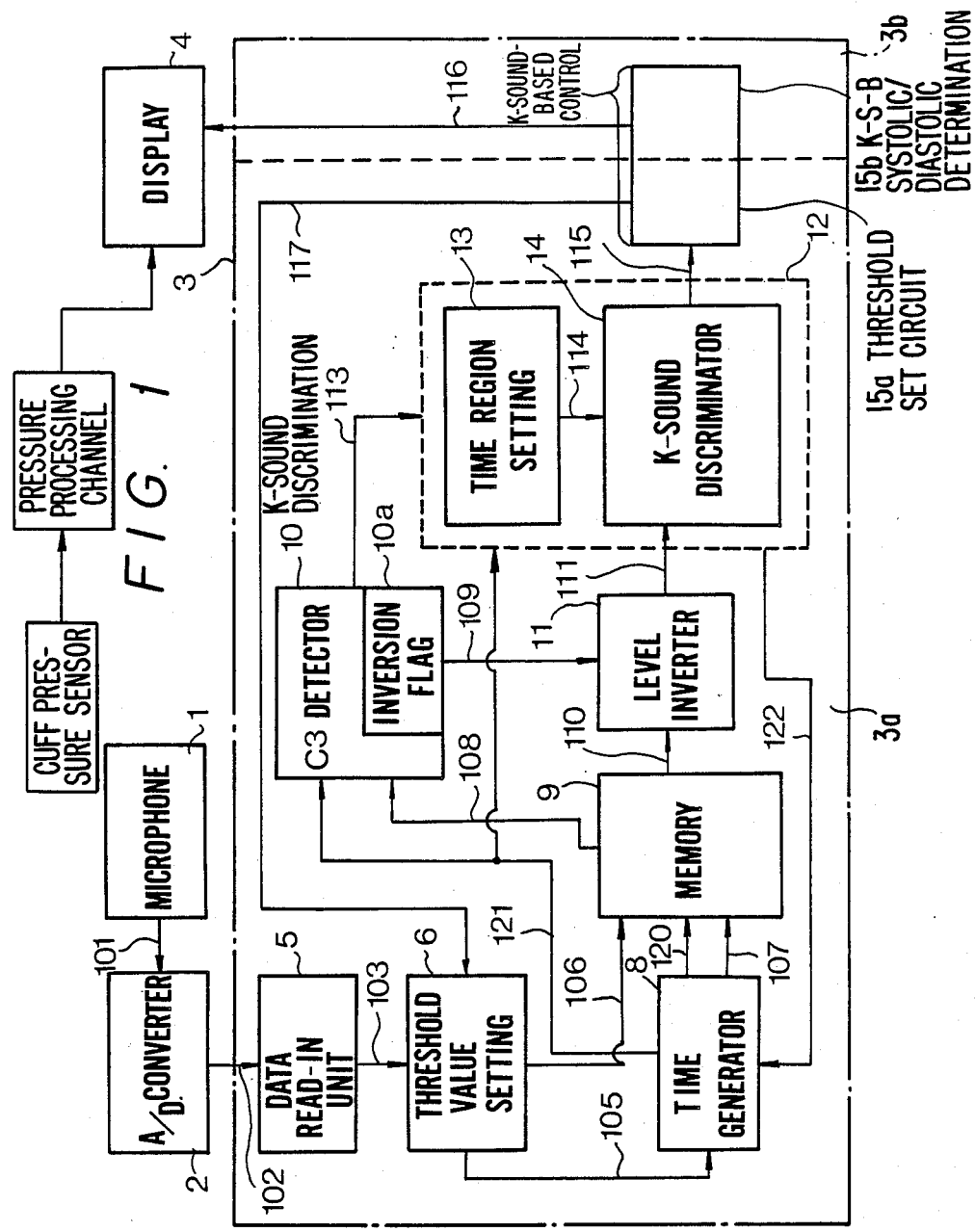

BLOOD PRESSURE MEASUREMENT APPARATUS

BACKGROUND OF THE INVENTION (1) Field of the Invention:

This invention relates to a blood pressure measurement apparatus and method in which a waveform discrimination method is used in the recognition of Korotkoff sounds in the measurement of blood pressure by auscultation.

(2) Description of the Prior Art:

In the detection of Korotkoff sounds according to the prior art, the most widespread approach is a discrimination method using a filter and comparator. This is referred to as the filter comparator method. Another approach used much less widely is a discrimination method, namely a pattern recognition method, which is based on the waveform of the Korotkoff sounds.

It is known that the spectral distribution of Korotkoff sounds generally has a frequency component different from body movement and external noise. The filter comparator method utilizes this fact and measures blood pressure by filtering a signal detected by a microphone attached to a pressure cuff fastened to a patient's arm, reducing the amplitude of frequency components other than the frequency component of the Korotkoff sounds, then comparing the frequency component of the Korotkoff sounds with a preset threshold value by means of a voltage comparator, and discriminating this frequency component based on its magnitude.

However, the frequency component of Korotkoff sounds not only varies from one patient to another but also differs for one and the same patient depending upon such measurement conditions as the time at which measurement is made and cuff pressure. Moreover, since the frequency band of interest is fairly wide, ranging from several tens of Hertz to 200–300 Hz, it is very difficult to extract solely the Korotkoff sound component by removing the sound of the patient's pulse and noise.

When the frequency component of the Korotkoff sounds is small in comparison with the sound of the patient's pulse, it is difficult to distinguish between the pulse sound and the Korotkoff sounds. Furthermore, since the discrimination is made based on a voltage level, measurement precision is readily influenced by any disparity in the amplitude of the Korotkoff sounds.

The aforementioned pattern recognition method in which discrimination is made based on the waveform of the Korotkoff sounds has recently been put into partial practical use.

In general, the waveform of a Korotkoff sound is as shown in FIG. 2(A). The waveform is subjected to an A-D conversion so as to make it easier to process the sound data detected by a pick up, with the digital signal resulting from the conversion being stored in means such as a memory. This is referred to as pattern detection processing. Next, maximum and minimum values are calculated from the stored signal values. For example, characteristic points are successively detected, as shown at C1, C2, C3, C4 in FIG. 3(A), four of such points being the minimum number necessary. This is referred to as a characteristic point plotting step. After the characteristic points have been detected, the general position of each characteristic point is verified and a decision is rendered as to whether the waveform is indeed indicative of a Korotkoff sound. This step is referred to as a discrimination processing step. Thus, recognition processing is divided into three process blocks.

If a characteristic point is not detected in the characteristic point plotting processing step, the pattern detection processing step is returned to for further signal read in. If a decision is rendered in the discrimination step to the effect that the waveform is not that of a Korotkoff sound, processing is executed for detecting further characteristic points or for reading in a new signal.

The relationship among the pattern recognition processing blocks is illustrated in FIG. 6.

A problem encountered in the pattern recognition approach is that in the actual measurement data obtained from a living body, a fine ripple shown in FIG. 7 tends to be produced in the vicinity of the maximum and minimum points of the Korotkoff sound signal owing to the influence an A-D conversion error.

Accordingly, with the method of detecting maximum and minimum values one by one while traversing the signal waveform in regular order and then treating each such value as a characteristic point, there is very large amount of feedback from the discrimination processing and, hence, the method requires a considerable period of time for execution. In addition, there is strong possibility that characteristic points will be detected erroneously.

SUMMARY OF THE INVENTION

Accordingly, an object of the present invention is to provide a blood pressure measurement apparatus and method adapted to detect a maximum value or minimum value of an extreme point capable of being traversed by a Korotkoff sound signal constituent within a predetermined time region in which detected characteristic points of detected blood vessel information serve as a reference, perform a Korotkoff sound recognition by comparing characteristic points, and recognize Korotkoff sounds accurately without the influence of a ripple component produced in the vicinity of the extreme values of the Korotkoff sounds.

Another object of the present invention is to provide a blood pressure measurement apparatus and method in which a Korotkoff sound recognition is performed with detected characteristic points serving as a reference, whereby extreme value points having the greatest certainty of being detected in a Korotkoff signal waveform can be treated as reference characteristic points.

According to the present invention, the foregoing objects are attained by providing a blood pressure measurement apparatus comprising: blood vessel information detecting means for detecting a signal waveform of a sound or vibration produced by a blood vessel; holding means for holding the signal waveform detected by the blood vessel information detecting means; maximum point detecting means for detecting a maximum point (C3) of the waveform held by the holding means; first C-point detecting means for detecting a minimum value point (C2) within a predetermined time region ($t_1$) the final instant of which is the maximum point (C3) detected by the maximum point detecting means; first discriminating means for discriminating whether a level difference between the minimum value point (C2) detected by the first C-point detecting means and the maximum point (C3) falls within a predetermined range; second C-point detecting means for detecting a maximum value point (C1) within a predetermined time region ($t_2$) the final instant of which is the detected minimum value point (C2), this being performed when the first discriminating means discriminates that the level difference falls within the predetermined range; second discriminating means for discriminating whether a level difference between the maximum value point (C1) detected by the second C-point detecting means and the minimum value point (C2) falls within a predetermined range; third C-point detecting means for detecting a minimum value point (C4) within a predetermined time region ($t_3$) the starting instant of which is the maximum point (C3), this being performed when the second discriminating means discriminates that the level difference falls within the predetermined range; third discriminating means for discriminating whether a level difference between the minimum value point (C4) detected by the third C-point detecting means and the maximum point (C3) falls within a predetermined range; and a control unit for starting at least the three C-point detecting means and three discriminating means, advancing control successively when the respective conditions are realized, and recognizing a Korotkoff sound in the signal waveform when the third discriminating means discriminates that the level difference between the minimum value point (C4) and maximum point (C3) falls within the predetermined range.

According to a preferred embodiment of the present invention, the control unit includes control means for restarting control from detection of the maximum point (C3) when the discrimination condition for any of the level discriminating means fails to be satisfied, and the blood vessel sound detecting means includes setting means for setting a threshold value of a detection signal in accordance with the magnitude of a Korotkoff sound recognized immediately before.

Further, the control unit includes holding means for holding the signal waveform at every predetermined time.

The foregoing objects may also be attained by providing a blood pressure measurement apparatus comprising: blood vessel information detecting means for detecting a signal waveform of a sound or vibration produced by a blood vessel; holding means for holding the signal waveform detected by the blood vessel information detecting means; minimum point detecting means for detecting a minimum point (C3) of the waveform held by the holding means; first C-point detecting means for detecting a maximum value point (C2) within a predetermined time region ($t_1$) the final instant of which is the minimum point (C3) detected by the minimum point detecting means; first discriminating means for discriminating whether a level difference between the maximum value point (C2) detected by the first C-point detecting means and the minimum point (C3) falls within a predetermined range; second C-point detecting means for detecting a minimum value point (C1) within a predetermined time region ($t_2$) the final instant of which is the detected maximum value point (C2), this being performed when the first discriminating means discriminates that the level difference falls within the predetermined range; second discriminating means for discriminating whether a level difference between the minimum value point (C1) detected by the second C-point detecting means and the maximum value point (C2) falls within a predetermined range; third C-point detecting means for detecting a maximum value point (C4) within a predetermined time region ($t_3$) the starting instant of which is the minimum point (C3), this being performed when the second discriminating means discriminates that the level difference falls within the predetermined range; third discriminating means for discriminating whether a level difference between the maximum value point (C4) detected by the third C-point detecting means and the minimum point (C3) falls within a predetermined range; and a control unit for starting at least the three C-point detecting means and three discriminating means, advancing control successively when the respective conditions are realized, and recognizing a Korotkoff sound in the signal waveform when the third discriminating means discriminates that the level difference between the maximum value point (C4) and minimum point (C3) falls within the predetermined range.

The control unit includes control means for restarting control from detection of the minimum point (C3) when the discrimination condition for any of the level discriminating means fails to be satisfied.

The blood vessel sound detecting means includes setting means for setting a threshold value of a detection signal in accordance with the magnitude of a Korotkoff sound recognized immediately before.

The apparatus further includes inverting means for inverting, with respect to a reference level, a signal waveform held by detection of the minimum point by the minimum point detecting means, wherein a value of an output inverted by the inverting means is used as a reference for maximum/minimum value detection and level discrimination performed by at least the three C-point detecting means and three discriminating means.

The control unit includes holding means for holding the signal waveform at every predetermined time.

Further, according to the present invention, there is provided a blood pressure measurement method which comprises: a blood vessel information detecting step for detecting a signal waveform of a sound or vibration produced by a blood vessel; a holding step for holding the signal waveform detected at the blood vessel information detecting step; a maximum point detecting step for detecting a maximum point (C3) of the waveform held at the holding step; a first C-point detecting step for detecting a minimum value point (C2) within a predetermined time region ($t_1$) the final instant of which is the maximum point (C3) detected at the maximum point detecting step; a first discriminating step for discriminating whether a level difference between the minimum value point (C2) detected at the first C-point detecting step and the maximum point (C3) falls within a predetermined range; second C-point detecting means for detecting a maximum value point (C1) within a predetermined time region ($t_2$) the final instant of which is the detected minimum value point (C2), this being performed when it is discriminated at the first discriminating step that the level difference falls within the predetermined range; a second discriminating step for discriminating whether a level difference between the maximum value point (C1) detected at the second C-point detecting step and the minimum value point (C2) falls within a predetermined range; third C-point detecting step for detecting a minimum value point (C4) within a predetermined time region ($t_3$) the starting instant of which is the maximum point (C3), this being performed when it is discriminated at the second discriminating step that the level difference falls within the predetermined range; a third discriminating step for discriminating whether a level difference between the minimum value point (C4) detected at the third C-point detecting step and the maximum point (C3) falls within a predetermined range; and a step of starting at least the three C-point detecting steps and three discriminating steps, advancing control successively when the respective conditions are realized, and recognizing a Korotkoff sound in the signal waveform when it is discriminated at the third discriminating step that the level difference between the minimum value point (C4) and maximum point (C3) falls within the predetermined range.

The present invention further provides a blood pressure measurement method which comprises: a blood vessel information detecting step for detecting a signal waveform of a sound or vibration produced by a blood vessel; a holding step for holding the signal waveform detected at the blood vessel information detecting step; a minimum point detecting step for detecting a minimum point (C3) of the waveform held at the holding step; a first C-point detecting step for detecting a maximum value point (C2) within a predetermined time region ($t_1$) the final instant of which is the minimum point (C3) detected at the minimum point detecting step; a first discriminating step for discriminating whether a level difference between the maximum value point (C2) detected at the first C-point detecting step and the minimum point (C3) falls within a predetermined range; second C-point detecting means for detecting a minimum value point (C1) within a predetermined time region ($t_2$) the final instant of which is the detected maximum value point (C2), this being performed when it is discriminated at the first discriminating step that the level difference falls within the predetermined range; a second discriminating step for discriminating whether a level difference between the minimum value point (C1) detected at the second C-point detecting step and the maximum value point (C2) falls within a predetermined range; a third C-point detecting step for detecting a maximum value point (C4) within a predetermined time region ($t_3$) the starting instant of which is the minimum point (C3), this being performed when it is discriminated at the second discriminating step that the level difference falls within the predetermined range; a third discriminating step for discriminating whether a level difference between the maximum value point (C4) detected at the third C-point detecting step and the minimum point (C3) falls within a predetermined range; and a step of starting at least the three C-point detecting steps and three discriminating steps, advancing control successively when the respective conditions are realized, and recognizing a Korotkoff sound in the signal waveform when it is discriminated at the third discriminating step that the level difference between the maximum value point (C4) and minimum point (C3) falls within the predetermined range.

Other features and advantages of the present invention will be apparent from the following description taken in conjunction with the accompanying drawings, in which like reference characters designate the same or similar parts throughout the figures thereof.

BRIEF DESCRIPTION OF THE DRAWINGS

FIG. 1 is a block diagram illustrating the basic construction of a Korotkoff sound recognition apparatus embodying the present invention;

DESCRIPTION OF THE PREFERRED EMBODIMENT

Figure 2A:
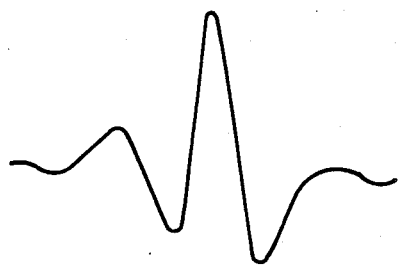
FIGS. 2(A) and 2(B) are views showing typical patterns of Korotkoff sounds.

An embodiment of the present invention will now be described in detail with reference to the drawings.

FIG. 1 is a block diagram illustrating the basic construction of an embodiment of the present invention. The arrangement includes a microphone 1 for picking up Korotkoff sounds (hereafter referred to as "K-sounds") and for producing an analog output signal indicative thereof. The input analog signal between range of 0.3 V and 2.0 V is converted into a 8 bit digital signal every 4 milliseconds (ms) by an analog-digital (A/D) converter 2 before being applied to an arithmetic circuit 3. The latter serves as recognition means and is adapted to recognize a K-sound by processing a series of sound data signals obtained in digital form from the A/D converter 2. The arithmetic circuit 3 comprises a one-chip CPU having a RAM and a ROM and is so illustrated that the various functions implemented by executing a program stored in the ROM are shown in block form. The present invention is capable of implementing these functions efficiently with the limited memory and limited processing time given the CPU. Numeral 4 denotes a display unit for displaying the fact that a K-sound has been recognized, for displaying other information as well.

The arithmetic circuit 3 includes a data read-in unit 5 for reading the digital output signal from the A/D converter 2 into the arithmetic circuit 3, a threshold value setting unit 6 which compares the newly read digital signal data from the data read-in unit 5 and the threshold value determined based upon the most recent K-sound. The arithmetic circuit 3 further includes a time generator for generating time information, and a memory (RAM) 9 for storing a digital data as well as the time information prevailing at the instant of detection. The threshold value which is to be held in the threshold value setting unit 6 is calculated from the most recent K-sound in a K-sound recognition unit 15 in accordance with the following equation, $$|C3-P_o|\cdot\beta 1, \tag{1}$$

where
C3: the characteristic point of the detected K-sound
$P_o$: reference level
$\beta 1$: one-third ($\frac{1}{3}$)
If the newly read digital signal is larger than the most recent threshold value, the sign bit is set to "1". This sign bit is included in the output 106. If, on the contrary, the new data is smaller than the threshold value, the sign bit is set to "0". After completion of this operation, the digital data signal containing the sign bit is delivered to the memory 9 as digital signal data 106. The sign bit is referred to by a C3 detector 10 in order to determine whether to produce a signal on line 113 or not.

Before continuing with the description of the functional blocks of the apparatus shown in FIG. 1, let us discuss typical patterns of the K-sounds which are to be recognized by the apparatus.

Figure 2B:

FIG. 2(A) is a typical pattern of a K-sound waveform recognized by the apparatus of the illustrated embodiment, and FIG. 2(B) illustrates the pattern when the signal level is inverted. As it is possible that the input waveform may represent two opposite waveforms, drawings illustrating the respective waveforms, for example, FIGS. 2(A) and 2(B), are provided in this application. The characteristic points of the K-sound waveform are the four points $C_1$–$C_4$ shown in FIGS. 3(A), (B). In order to help understanding of the present invention, level differences dP1 to dP3 and time regions $T_1$ to $T_3$ are labeled in FIG. 3A. They will be referred to in the following discussion. In the illustrated embodiment, a K-sound is recognized on the basis of the relationship among these four points.

Figure 3A:
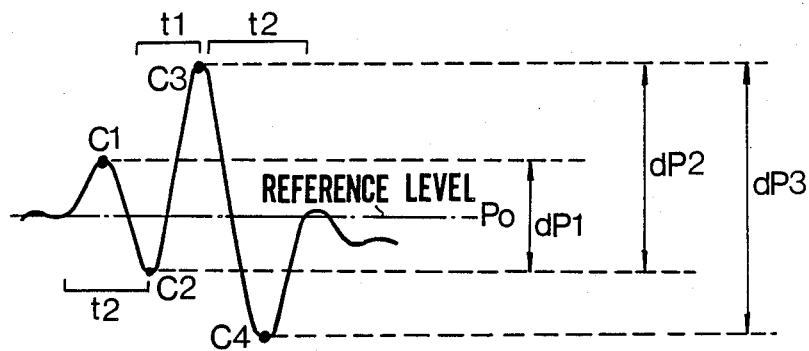
FIGS. 3(A) and 3(B) are views showing characteristic portions of a Korotkoff sound waveform.

In FIGS. 3(A), (B), the point C3 is defined as the point where the signal level attains an absolute extreme value, i.e., the highest peak or lowest valley, and is a portion which has great significance for the purpose of K-sound recognition, described below. Specifically, once the characteristic point C3 has been found, the characteristic points C1, C2, C4 are each obtained by a prescribed analytical method which starts from the point C3.

Each of the functional blocks described below constitutes means for recognizing the abovementioned K-sound waveform patterns both reliably and efficiently.

Returning to FIG. 1, numeral 10 is the C3 detector for detecting a relative (local) extreme value, i.e., a maximum value or minimum value in the digital signal data read out of the memory 9. Numeral 11 designates a level inverter which, for the purpose of K-sound recognition, inverts the level of the signal waveform data, which is read out of the memory 9, whenever necessary. A characteristic point detector 12 performs a predetermined calculation with regard to the signal waveform data read out of the memory 9 and time data to check for the presence of a waveform located at each of the characteristic points C1, C2, C4. The characteristic point detector 12 comprises a time region setting unit 13 for generating prescribed time region data, and a K-sound discriminator 14 for discriminating whether sound data of a signal level forming a characteristic is present within the time region, and is adapted to detect each characteristic point in accordance with a predetermined calculation procedure, described below, when a signal indicating that the C3 point has been detected is received from the C3 detector 10. The output of the K-sound discriminator 14 is applied to a K-sound recognition unit 15, which examines the positional relationship among a collection of characteristic points found by the characteristic point detector 12, in order to recognize a K-sound.

The operation of the present embodiment comprising the foregoing elements will now be described.

The output of the microphone 1 is an analog electric signal 101 indicative of a K-sound picked up by the microphone. The signal 101 is converted into a digital signal 102 at every 4 ms sampling instant by the A/D converter 2. The digital signal 102 at the output of the A/D converter 2 is read into the arithmetic circuit 3 by the data read-in unit 5 and is applied to the threshold value setting unit 6 as a series of digital signal data 103 in a time series. The threshold value setting unit 6 sets a threshold value in dependence upon a signal 117 from the K-sound recognition unit 15 indicative of the magnitude of a K-sound which appeared last in accordance with equation 1. By setting the threshold value to $|C3-P_o|\cdot\beta 1$, the unit 6 reduces the influence of noise contained in the waveform data 103.

In order to suitably deal with a signal pattern input of any amplitude whatsoever at the start of measurement, no threshold value is set when measurement starts. After measurement starts, however, a threshold value is set upon predicting, from the magnitude of an immediately preceding K-sound, the smallest magnitude capable of being traversed by the next K-sound. More specifically, in a case where a K-sound has already appeared in the course of measurement, the threshold value setting unit 6 sets a threshold value in dynamic fashion in dependence upon the signal 117 from the K-sound discriminator 15 indicative of the magnitude of the threshold $|C3-P_o|\cdot\beta 1$, thereby making it possible to detect the C3 point accurately and rapidly.

Accordingly, the threshold value setting unit 6 in the apparatus of the illustrated embodiment is different in nature from threshold value setting means in the conventional comparator method, in which a threshold value is set that is fixed with respect to the amplitude of the K-sound. The threshold value setting unit 6 delivers the digital signal data 106 to the memory 9 each 4 ms interval and also delivers timing signal 105 to the time generator 8 each sampling instant at the A/D converter 2.

The time generator 8 is a unit which cyclically counts timing information that increases every millisecond, by way of example. When the timing signal 105 is received from the threshold value setting unit 6, the time generator 8 successively counts up a write-in address 120 of the memory 9 so that the digital signal data 106 from the threshold value setting unit 6 and prevailing clocked time information 107 are written into the memory in accordance with the counted up address. Thus, the digital signal value data 106 and the time information 107 prevailing at the moment of detection are stored in the memory 9.

The time generator 8 also outputs a read-out address 120 of the memory 9 at a predetermined time interval and produces a read enable signal 121 when a read-out becomes possible.

The digital signal data 106 stored in memory 9 is read by the C3 detector 10 and characteristic point detector 12 in accordance with the read enable signal 121, whereby K-sound recognition processing is performed. In order that the memory 9 can be read from any address when K-sound recognition processing is executed, the characteristic point detector 12 provides the time generator 8 with an address designating signal 122 for designating a read-out address from which a read-out is to be started.

The K-sound recognition processing will now be described with reference to the flowchart of FIGS. 4(A) and 4(B).

Figure 3B:
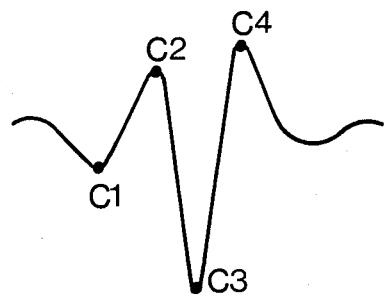

In accordance with the read enable signal 121 from the time generator 8, the C3 detector 10 reads sound data 108 out of the memory 9 in accordance with the successively stored time series, examines these data in regular order and executes processing for detecting the C3 point in the signal pattern shown in FIG. 3(A) or FIG. 3(B).

Figure 4:
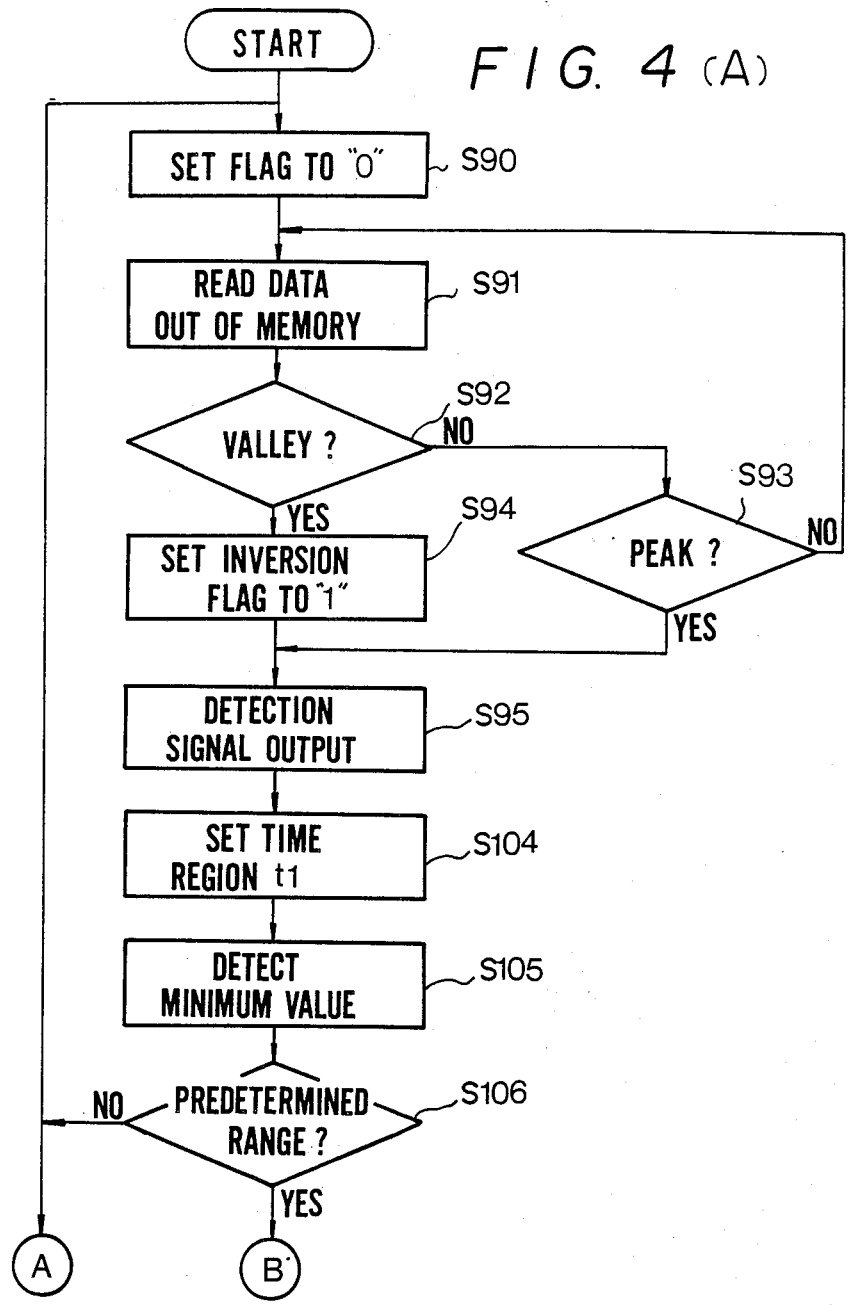
FIG. 4(A) and 4(B) is a flowchart illustrating processing extending from detection of each characteristic point of a Korotkoff sound to recognition of a Korotkoff sound according to an embodiment of the present invention.
Figure 4B:
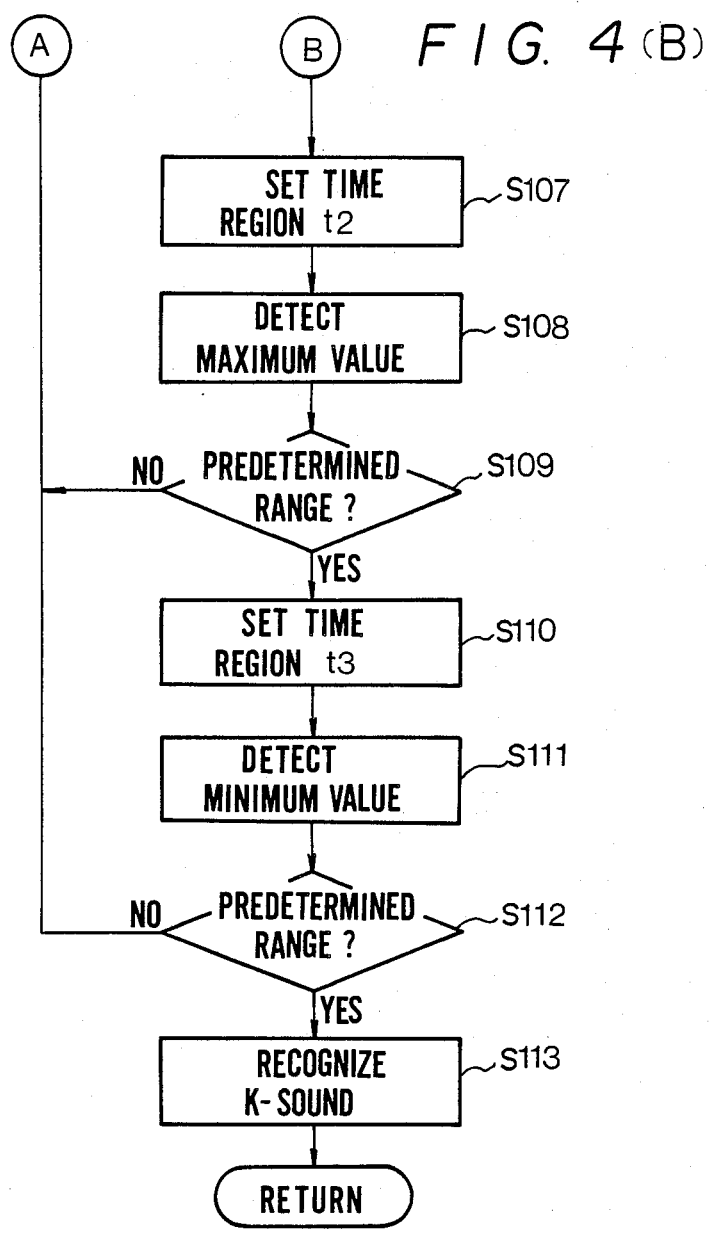

In the first step S90 of the flowchart shown in FIGS. 4(A) and (B), an inversion flag 10a internally of the C3 detector 10 is set to "0". When the inversion flag 10a is "0", an inversion indicating signal 109 is reset; when the flag 10a is "1", the inversion designating flag 109 is set. When the inversion indicating signal 109 is in the reset state, the level inverter 11 delivers read-out data 110 from memory 9 directly to the characteristic point detector 12 as output data 111. When the inversion indicating signal 109 is in the set state, the level inverter 11 inverts the read-out data from the memory 9 and delivers the result to the characteristic point detector 12 as the output data 111.

Initially, the inversion flag 10a is set to "0" and the inversion designating signal 109 is reset. Consequently, the read-out data from memory 9 is applied as such to the characteristic point detector 12.

Next, at a step S91, the C3 detector 10, in accordance with the read enable signal 121, reads the digital signal data 106 from the threshold value setting unit 6 stored successively in memory 9 via, the A/D converter 2 out of the memory in the same order in which it was stored and compares this with digital signal data 106 read out immediately before. The time generator 8 exercises read-out control separate from the write-in of the digital signal data 106. The reading of data from the memory 9 can be performed immediately by writing in the digital signal data 106 by means of the threshold value setting unit 6. Extreme value detection processing is executed from step S92 onward and is performed by a level comparison of digital signals at three consecutive points in the sound data 108.

Thus, at the step S92, digital signals at three consecutive points are compared to determine whether a valley point has been detected, that is, to check whether the level difference between adjacent ones of the points changes from a decreasing value to an increasing value. If a valley point is detected and this valley point is given a sign bit "1", that is the newly obtained digital signal data is determined by the C3 detector 10 to be larger than the current threshold value, this point is treated as being the characteristic point C3 and the program proceeds from the step S92 to a step S94, at which the inversion flag 10a is set to "1" and the inversion indicating signal 109 is delivered to the level inverter 11. The program then proceeds to a step S95.

When the inversion indicating signal 109 is delivered to the level inverter 11, K-sound detection is performed. To this end, the level of each item of waveform data 110 corresponding to the characteristic points $C_1$–$C_4$ in FIG. 3(B) and read out of the memory 9 is inverted with regard to a base line [level $P_o$ shown in FIGS. 5(D), (E)] that will turn these levels into the signal pattern shown in FIG. 3(A). The inverted levels are delivered to the characteristic point detector 12.

If a valley point is not detected at the step S92, the program proceeds to a step S93, at which it is determined whether a peak C3 has been detected, that is, whether the level difference between adjacent ones of the three consecutive points changes from an increasing value to a decreasing value. If a peak is detected, this peak is determined as to whether the peak is exceeding the threshold value with referring to the sign bit included in the digital signal data 106. If the peak is exceeding the threshold value, the peak is treated as being the characteristic point C3 and the program proceeds to a step S95. If a peak is not detected at the step S93, the program returns to the step S91, the next item of digital signal data is read and processing for detecting a characteristic point C3 is performed again.

If a peak point is detected at the step S93, the inversion flag 10a remains at "0" and the program proceeds to the step S95. This step calls for a characteristic point detection signal 113 to be sent from the C-point detector 10 to the characteristic point detector 12 to indicate that the detected point is a characteristic point. The program then proceeds to a step S104.

Figure 5A:
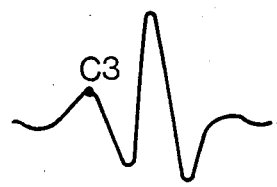
FIGS. 5(A) to 5(O) are views illustrating the recognition states of each characteristic point of a Korotkoff sound waveform when the processing indicated by the flowchart of FIG. 4 is executed.

If a K-sound is recognized, what is detected first is the peak point. An example of the state in which the initial peak is detected is illustrated in FIG. 5(A).

In response to the characteristic point detection signal 113 from the C3 detector 10 indicating that the C3 point has been detected, the characteristic point detector 12 initiates detection of each characteristic point of the digital signal data constituting a K-sound. This being performed by processing from step S104 onward.

When the characteristic point detection signal 113 is received, the characteristic point detection circuit 12 produces the address designating signal 122 so that data stored in the memory 9 prior to detection of the characteristic point are read out of the memory sequentially in the same order that the data were stored. These data are stored in a RAM. In other words, each item of data from C1 to C3 is stored every 4 ms sampling period in the RAM at the instant C3 is detected.

Figure 5B:
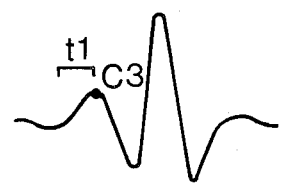

The step S104 calls for the time region setting unit 13 to set a predetermined time region $t_1$ the final instant of which is the position of C3. The unit 13 produces a time region signal 114 indicative of this time region and applies the signal to the K-sound discriminator 14. The setting of this time region can be accomplished by storing in a ROM a predetermined value in accordance with the figures given in below. The set time region $t_1$ is illustrated in FIG. 5(B). According to the embodiment of the present invention, each time region $t_1$, $t_2$ and $t_3$ have the values $t_1=10$, $t_2=15$ and $t_3=15$ [×4 ms]. And these time region data have been stored previously in the ROM which is constituting the time region setting unit 13.

Figure 5C:
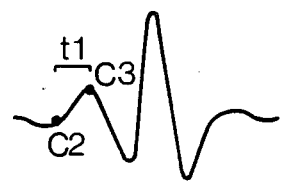

Next, the program proceeds to a step S105, at which the K-sound discriminator 14 reads digital signal data within the time region $t_1$ set by the time region setting unit 13 and stored in the RAM, detects a minimum value within the read data and treats this value as C2 [FIG. 5(C)]. The minimum level point is detected by comparing the levels of two points in the output data 111 from the level inverter 11. Next, a step S106 calls for a decision as to whether the level difference (dP2) between C2 and C3 falls within a predetermined range. The upper and lower limits of this range are stored beforehand in the ROM in accordance with the below table. According to the embodiment of the present invention, each level difference dP1, dP2 and dP3 is given as follows.

|  | lower limit | upper limit |
| --- | --- | --- |
| dP2 | 15 | — |
| dP1 | dP2 × α1 | dP2 × α2 |
| dP3 | dP1 × α3 | dP2 × α4 |

In the above table, the unit is 0.7 V/256 and also, the level differences illustrated in FIG. 3A, dP1, dP2 and dP3, are given below.

dP1: voltage difference between C1 and C2
dP2: voltage difference between C3 and C2
dP3: voltage difference between C3 and C4

In FIG. 5(C), the level difference is not within the predetermined range, so that the program returns to the step S90 for detection of the next characteristic point.

Figure 5D:
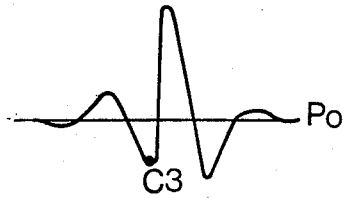
Figure 5E:
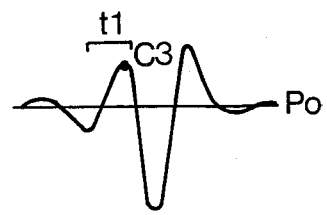
Figure 5F:
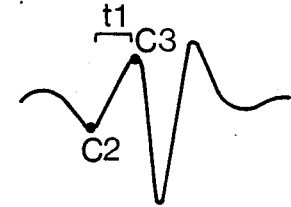
Figure 5G:
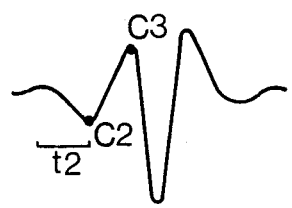

A valley point shown in FIG. 5(D) is detected by subsequent C3 detection processing. The program proceeds from the step S92 to the step S94, the inversion flag $10a$ is set and, in the data read out of the memory 9 and stored in the RAM, the input signal level is level-converted from P to $2P_0 - P$ (where $P_0$ is a reference level) by the level inverter 11, thereby giving the waveform shown in FIG. 5(E). Thus, the signal waveform is apparently inverted. Next, the minimum point C2 is detected within the set time region $t_1$ through the steps S104, S105 [FIG. 5(F)]. The decision step S106 now finds that the point C2 lies within the predetermined limits, so that the program proceeds from this step to a step S107, where the time region setting unit 13 sets a predetermined time region $t_2$ the final instant whereof is the position of C2. A signal 114 indicative of this time region is delivered to the K-sound discriminator 14. The set time region $t_2$ is shown in FIG. 5(G).

Figure 5H:
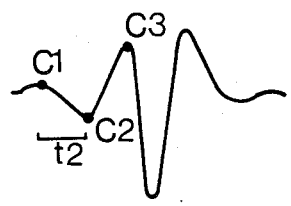

Next, the program proceeds to a step S108, at which the point (value) of a maximum level is detected within the time region $t_2$ and treated as C1. The detection of the maximum level is performed by comparing the level between two points. This is followed by a step S109, at which it is determined whether the level difference dP1 between C1 and C2 lies with a predetermined range. In FIG. 5(H), detection of C1, C2, C3 is judged to be improper and the program returns to the step S90.

Figure 5I:
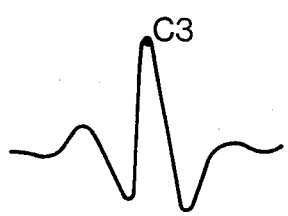
Figure 5J:
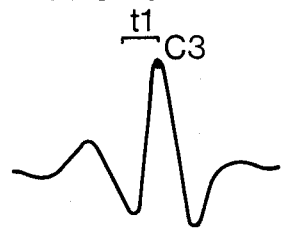
Figure 5K:
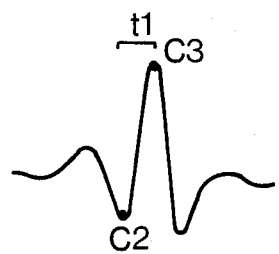
Figure 5L:
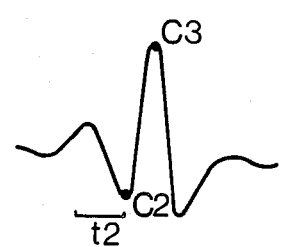
Figure 5M:
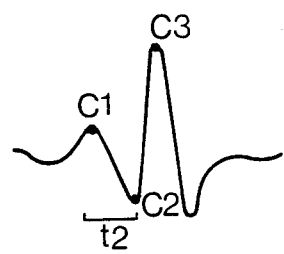

The characteristic point detected next is C3 shown in FIG. 5(I) and no inversion is made of the read waveform by the level inverter 11. At the step S104, the time region $t_1$ is set as shown in FIG. 5(J), the characteristic point C2 shown in FIG. 5(K) is detected at the step S105, the time region $t_2$ having the characteristic point C2 as its final instant is set at the step S107, as shown in FIG. 5(L), and the maximum value C1 is detected within the time region $t_2$ shown in FIG. 5(M) at the step S108. This is followed by the level decision step S109, at which it is judged that detection of C1, C2, C3 is proper.

Figure 5N:
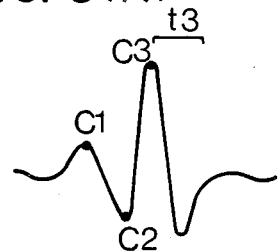
Figure 5O:
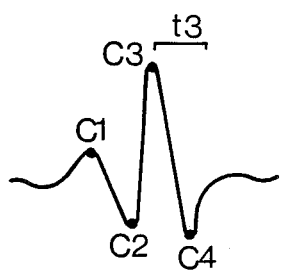
Figure 6:
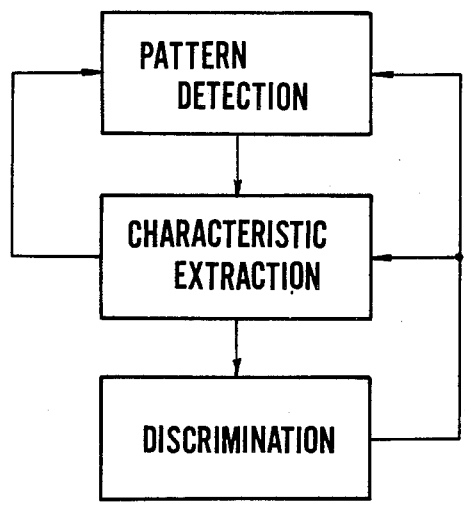
FIG. 6 is a block diagram illustrating a conventional Korotkoff sound discrimination method based on waveform configuration.

The program then proceeds to a step S110, at which the time region setting unit 13 sets a time region $t_3$ the final instant of which is the position of C3, as shown in FIG. 5(N). Next, at a step S111, a digital signal data 103 within the time region $t_3$ is read out of the memory 9, the point of a minimum level is detected and the point is treated as being C4. This is shown in FIG. 5(O). This is followed by a step S112, at which it is determined whether the level difference dP3 between C3 and C4 falls within a predetermined range.

If the level difference does not fall within the predetermined range, the program returns to the step S90. If the level difference does fall within the predetermined range, the signal is recognized to be a K-sound at a step S113.

Figure 7:
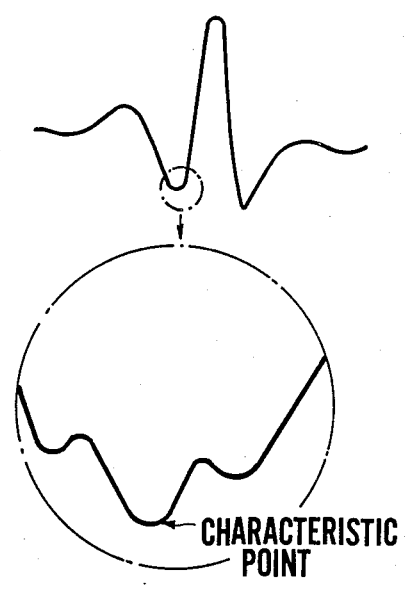
FIG. 7 is a view showing a Korotkoff signal waveform in which a small ripple is produced in the vicinity of extreme values.

Since the present method is a very simple method of detecting the characteristic points C1, C2, C3, C4, it is suited to real-time processing performed by a one-chip CPU. Furthermore, since the maximum value of a peak or the minimum value of a valley is detected within each predetermined time period, the influence of noise (FIG. 7) produced in the vicinity of extreme values of the K-sound waveform is almost nil.

When the K-sound discriminator 14 successively detects the positions C3, C2, C1 and C4, an output 115 is produced so as to inform the K-sound recognition unit 15 that the digital signal data should be treated as a K-sound. When the K-sound is recognized by the unit 15, the unit performs a computation adapting equation 1 to obtain and to deliver the new threshold value to the threshold value setting unit 6 in order to renew the current threshold value. The recognized K-sound is delivered from the K-sound recognition unit 15 to the display unit via line 116.

In the illustrated embodiment, an example has been described in which characteristic points are detected upon inverting peaks and valleys of the signal waveform as reference characteristic points whenever necessary. However, it is permissible to execute processing without making the inversion or to treat a reference characteristic point solely as the waveform peak. In such case, the inversion flag and level inverter 11 can be deleted.

ADVANTAGES OF THE INVENTION

According to the present invention as described above, the characteristics of a K-sound waveform are investigated directly. As a result, it is unnecessary to place a restriction upon the frequency band characteristic of a filter or to set a threshold value fixed with respect to the amplitude of a K-sound, as in the prior art. Moreover, measurement precision is not readily influenced by the frequency component constituting the K-sound or by the effect of a disparity in the amplitude of the K-sound.

Further, according to the present invention, the maximum value or minimum value capable of being traversed by a K-sound signal constituent is detected within each set time region, unlike the conventional method in which maximum and minima are detected one by one while traversing the waveform in regular order. Accordingly, the detection of candidates for characteristic points can be readily performed by a very short program and measurement precision is not influenced by fine ripple produced in the vicinity of extreme values of a K-sound waveform, particularly ripple due to a conversion error which readily occurs after the A/D conversion.

According to the present invention, a plurality of signal patterns indicative of K-sounds can be recognized efficiently on a real-time basis in the limited memory and processing time given a one-chip CPU by using simple software programmed in such a manner that typical patterns of K-sound waveforms are recognized. By adopting an arrangement in which level inverting means is provided, a plurality of patterns can be recognized by a short program.

As many apparently widely different embodiments of the present invention can be made without departing from the spirit and scope thereof, it is to be understood that the invention is not limited to the specific embodiments thereof except as defined in the appended claims.

What is claimed is:

1. A blood pressure measurement apparatus, comprising:
   blood vessel information detecting means for detecting vibration of a blood vessel to produce a signal waveform;

storage means for storing the signal waveform produced by said blood vessel information detecting means and time information associated with the signal waveform;

reference absolute extreme value point locating means for operating on the signal waveform stored in said storage means in response to a conditional command to locate a reference absolute extreme value point of the signal waveform stored in said storage means, the reference extreme value point used as a base point for time duration measurement, said reference absolute extreme value point locating means comprising:

first extreme value detecting means for detecting one of first and next extreme value points in the signal waveform stored in said storage means;

polarity determining means for determining polarity of the one of the first and next extreme value points and for inverting a local portion of the signal waveform when the polarity is negative; and means for providing as an output the reference absolute extreme value point representative of the one of the first and next extreme value points detected by said first extreme value detecting means;

C-point value searching means, responsive to the time information and to the output of said reference absolute extreme value point means, for finding relative extreme value points with respect to the reference extreme value point in the signal waveform stored in said storage means to thereby validate existence of a Korotkoff waveform, said C-point value searching means comprising:

means for receiving the local portion of the signal waveform stored in said storage means;

second extreme value detecting means for detecting the relative extreme value points in the local waveform portion in predeterined time intervals referenced to the reference absolute extreme value point in the signal waveform stored in said storage means, and for providing an occurrence output indicative thereof; and level determining means for determining whether level differences between adjacent ones of the reference absolute and relative extreme value points fall within predetermined ranges and for providing level difference outputs indicative thereof; and control means, responsive to said seocnd extreme value detecting means and said level determining means, for providing the conditional command to said reference absolute extreme value point locating means to detect the next extreme value point when the occurrence and level difference outputs indicate absence of at least one of occurrence and level differences within the predetermined ranges and for providing an output indicative of the existence of a Korotkoff sound waveform when the occurrence and level difference outputs indicate both occurrence and level differences within the predetermined ranges.

2. An apparatus according to claim 1, wherein said blood vessel information detecting means includes setting means for setting a threshold value for detection of the vibration of the blood vessel in accordance with the magnitude of the representation of a Korotkoff sound recognized immediately before.

3. An apparatus according to claim 1, wherein said storage means periodically stores a portion of the signal waveform using a predetermined time period.

4. A blood pressure measurement method, comprising the steps of:

(a) detecting vibration of a blood vessel to produce a signal waveform;

(b) storing the signal waveform produced in step (a) together with time information associated therewith;

(c) operating on the signal waveform stored in step (b) in response to a conditional command to locate a reference absolute extreme value point of the signal waveform, the reference extreme value point being used as a base point for time duration measurement, step (c) comprising the steps of:

(ci) detecting one of first and next extreme value points in the signal waveform stored in step (b);

(cii) determining polarity of the one of the first and next extreme value points and inverting a local portion of the signal waveform when the polarity is negative; and (ciii) providing the reference absolute extreme value point representative of the one of the first and next extreme value points detected in step (ci);

(d) finding relative extreme value points with respect to the reference extreme value point and the time information to validate existence of a Korotkoff waveform, comprising the steps of:

(di) receiving the local portion of the signal waveform;

(dii) detecting the relative extreme value points in the local waveform portion in predetermined time intervals referenced to the reference absolute extreme value point in the signal waveform stored in step (b) and providing an occurrence output indicative thereof; and (diii) determining whether level differences between adjacent ones of the reference absolute and relative extreme value points fall within predetermined ranges and providing level difference outputs indicative thereof;

(e) providing the conditional command for step (c) to detect the next extreme value point when the occurrence and level difference outputs indicate absence of at least one of occurrence and level differences within the predetermined ranges; and (f) providing an output indicative of the existence of a Korotkoff sound waveform when the occurrence and level difference outputs indicate both occurrence and level differences within the predetermined ranges.

* * * * *